United States Patent
Böttcher et al.

(10) Patent No.: US 6,573,400 B1
(45) Date of Patent: Jun. 3, 2003

(54) PREPARATION OF 2-KETO-L-GULONIC ESTERS

(75) Inventors: Andreas Böttcher, Nussloch (DE); Wolfram Burst, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 181 days.

(21) Appl. No.: 09/636,825

(22) Filed: Aug. 14, 2000

(30) Foreign Application Priority Data

Aug. 19, 1999 (DE) .......................... 199 38 980

(51) Int. Cl.⁷ .............................................. C07C 69/66
(52) U.S. Cl. ........................................ 560/174; 560/186
(58) Field of Search ................................. 560/174, 186

(56) References Cited

U.S. PATENT DOCUMENTS

| | | | |
|---|---|---|---|
| 2,462,251 A | * 2/1949 | Bassford et al. | 549/315 |
| 2,491,933 A | 12/1949 | Ruys et al. | 260/338 |
| 3,951,945 A | * 4/1976 | Heesen et al. | 536/18.2 |
| 4,180,511 A | * 12/1979 | Crawford | 549/315 |
| 5,118,833 A | * 6/1992 | Mori et al. | 560/51 |
| 5,128,487 A | 7/1992 | Tomislav et al. | 549/315 |
| 5,227,515 A | * 7/1993 | Sokukawa et al. | 560/174 |
| 5,391,770 A | * 2/1995 | Le Fur et al. | 549/315 |
| 5,744,618 A | * 4/1998 | Fechtel et al. | 549/315 |
| 5,744,634 A | 4/1998 | Veits | 560/174 |
| 6,028,215 A | 2/2000 | Bessling et al. | 560/265 |

FOREIGN PATENT DOCUMENTS

| | | |
|---|---|---|
| DE | 39 696 | 6/1965 |
| DE | 198 29 809 | 1/1999 |
| EP | 403 993 | 12/1990 |
| EP | 535 927 | 4/1993 |
| EP | 671 405 | 9/1995 |
| GB | 1 222 322 | 2/1971 |
| PL | 57042 | 11/1968 |
| PL | 57573 | 11/1968 |
| WO | WO 97/43433 | 11/1997 |
| WO | WO 99/03853 | 1/1999 |

OTHER PUBLICATIONS

Reichstein et al. "Eine Ergriebige Synthese der 1–Ascorbinsäure (C–Vitamin)²)" Helvitica Chem. Acta vol. 17, (1934) pp. 311–328.

Ullmanns Encyklopädie der technischen Chemie vol. 2(1972) pp. 516, 533–537, 652–660 and vol. 3(1973) pp. 386–388.

Popelier "Contribution à Pétude des sulfates acides d'alkyle" Bulletin de la Société Chimique de Belgique vol. 35 (1926) pp. 264–277.

* cited by examiner

Primary Examiner—Alan L. Rotman
Assistant Examiner—Taylor V. Oh
(74) Attorney, Agent, or Firm—Keil & Weinkauf

(57) ABSTRACT

$C_1$–$C_{10}$-alkyl 2-keto-L-gulonates are prepared by esterifying 2-keto-L-gulonic acid or diacetone-2-keto-L-gulonic acid with a $C_1$–$C_{10}$-alcohol in the presence of an acidic catalyst by a process in which the esterification is carried out in a liquid film on a hot surface with simultaneous removal of water.

10 Claims, No Drawings

PREPARATION OF 2-KETO-L-GULONIC ESTERS

The present invention relates to a novel process for the preparation of 2-keto-L-gulonic esters. These esters are important intermediates for the synthesis of L-ascorbic acid (vitamin C).

The esterification of 2-keto-L-gulonic acid with a lower alcohol, in particular methanol, is known from numerous publications.

In this type of reaction, the yield is limited in principle by the equilibrium in the esterification reaction. The esterification thus benefits from an excess of alcohol or from continuous removal of the resulting water, which can be effected, for example, by azeotropic distillation.

In the conventional processes, including the Reichstein process, a long boiling time is usually chosen for achieving a high degree of esterification and hence a satisfactory yield. However, this impairs the purity, since both the 2-keto-L-gulonic acid and its methyl ester may form further byproducts under these conditions.

Various methods have been proposed for reducing the water content in the esterification. Water can be removed during the reaction by continuously distilling off the water/alcohol mixture, treating the distillate with molecular sieves and recycling the alcohol thus dried (Pol. Pat. 57042; Pol. Pat. 57573). Another possibility mentioned comprises distilling off the water/alcohol mixture continuously during the reaction and replacing it with fresh dry alcohol (EP-A-0 535 927). In both cases, a large amount of alcohol must be distilled off, with a correspondingly high energy consumption. Moreover, reaction times of up to 10 hours are necessary, with the danger of decomposition and secondary reactions.

EP-A-0 671 405 describes a process for the preparation of methyl or ethyl 2-keto-L-gulonate by esterifying 2-keto-L-gulonic acid with methanol or ethanol, respectively, in the presence of an acidic ion exchanger. The reaction is carried out in a tubular reactor filled with ion exchange resin, for an average residence time of the reactants of from 10 to 120 minutes.

EP-A-0 403 993 describes a process for the preparation of methyl 2-keto-L-gulonate, in which the esterification is carried out only partially, i.e. not until the equilibrium of the esterification reaction is reached. In an intermediate stage, unesterified 2-keto-L-gulonic acid and impurities present are precipitated by adding sodium bicarbonate or potassium bicarbonate—in an amount just sufficient essentially for neutralizing the ester solution—and are separated off.

In a process described in WO 99/03853, 2-keto-L-gulonic acid is converted into 2-keto-L-gulonic ester in a two-stage esterification process, the solution formed after the first esterification step being at least partly evaporated down to remove the resulting water of reaction, and the residue formed being subjected to a second esterification process.

WO 97/43433 and U.S. Pat. No. 5,391,770 describe the synthesis of butyl 2-keto-L-gulonate by refluxing 2-keto-L-gulonic acid in butanol for several hours in the presence of p-toluenesulfonic acid and then crystallizing out the desired product by cooling the reaction mixture.

DE-A-198 29 809 relates to a process for the preparation of esters from alcohol and carboxylic acid by means of a catalyst and isolation of the ester in a rectification column provided with internals.

For diacetone-2-keto-L-gulonic acid (DAK), the reaction product of the classical Reichstein process [Reichstein and Grüssner, Helv. Chim. Acta 17, (1934), 311], U.S. Pat. No. 2,491,933 mentions an esterification with elimination of acetone. The acetone formed is removed as a low boiler via the top of the distillation column.

The abovementioned esterification methods are moreover suitable only to a limited extent for a continuous procedure. Methods for a continuous procedure have been described only for the methyl and the ethyl ester of 2-keto-L-gulonic acid. Even under optimized conditions, average residence times of more than 10 minutes are required in all these reactions. In addition, an excessively high residual water content is still measured in the reaction mixture. In some subsequent reactions of the ester, for example for a vitamin C synthesis, this is generally not desired.

It is an object of the present invention to provide a process for the preparation of 2-keto-L-gulonic esters which does not have the abovementioned disadvantages.

We have found that this object is achieved by a process for the preparation of $C_1$–$C_{10}$-alkyl 2-keto-L-gulonates by esterifying 2-keto-L-gulonic acid or diacetone-2-keto-L-gulonic acid with a $C_1$–$C_{10}$-alcohol in the presence of a acidic catalyst, wherein the esterification is carried out in a liquid film on a hot surface with simultaneous removal of water.

In the above definition of the subject of the invention, the term "liquid film" includes the thin liquid or flowable films or layers formed by the reaction mixture and having a thickness of from 0.05 to 10 mm, preferably from 0.05 to 5 mm, particularly preferably from 0.1 to 2 mm. Such thin layers are produced, for example, by allowing the liquid reaction mixture to trickle down, by the action of centrifugal force or by especially designed wipers on the heated surfaces. Typical apparatuses for producing such thin layers include falling-film or downflow evaporators, Sambay and Luwa thin-film evaporators [evaporators in which thin liquid films are produced by means of rotating wiper blades or rollers], rotary evaporators and thin-film rectification columns [e.g. packed columns and film columns, rectifiers having rotating inserts (spray columns)]. A more detailed description of the reactors mentioned here is to be found in Ullmanns Encyklopädie der technischen Chemie, 4th Edition, Volume 2 (1972), pages 516, 533–537 and 652–660 and in Volume 3 (1973), pages 386–388.

In principle all $C_1$–$C_{10}$-alcohols are suitable for the esterification, advantageously saturated, branched or straight-chain alkyl alcohols having 3 or more carbons, preferably alcohols having an alkyl radical of 3 to 10 carbons atoms, for example n-propanol, isopropanol, 1-butanol, 2-butanol, 2-methyl-1-propanol, 2-methyl-2-propanol, 1-pentanol, 2-pentanol, 3-pentanol, 1-hexanol, 2-hexanol, 1-heptanol, 2-heptanol, 1-octanol, 2-octanol, 3-octanol, 1-nonanol, 2-nonanol, 1-decanol, 2-decanol and 4-decanol, particularly preferably $C_3$–$C_8$-alcohols selected from the group consisting of n-propanol, isopropanol, 1-butanol, 2-butanol, 2-methyl-1-propanol, 2-methyl-2-propanol, 1-pentanol, 1-hexanol and 1-octanol. Very particularly preferred alcohols are n-butanol and n-pentanol.

The alcohol is used in a 2- to 10-fold, preferably 3- to 8-fold, preferably 4- to 6-fold molar excess, based on the particularly 2-keto-L-gulonic acid or diacetone-2-keto-L-gulonic acid used.

In the course of the esterification reaction, both the water present as solvent and the water additionally formed in the esterification can be removed from the reaction space as a lower-boiling azeotropic mixture via the gas phase.

If required, phase separation (alcohol/water) can be carried out after the condensation, with recycling of the esterification alcohol. However, complete dewatering of the recycled alcohol, for example by membrane methods or by distillation, is as a rule not necessary since, according to the invention, complete dewatering takes place in the reaction space.

In the esterification of 2-keto-L-gulonic acid with $C_1$–$C_3$-alcohols, undesired losses of alcohols and hence lower yields may occur in the removal of water by distillation, owing to the low boiling points of these alcohols. The esterification rate can be increased again by appropriately replenishing the alcohol losses during the reaction.

By adding an acidic catalyst, the esterification reaction is catalyzed in a manner known per se. The catalyst is used in amounts of from 0.001 to 0.2, preferably from 0.005 to 0.1, particularly preferably from 0.005 to 0.05, mol per mole of 2-keto-L-gulonic acid or diacetone-2-keto-gulonic acid.

As a rule, all homogeneous or heterogeneous acidic catalysts known per se may be used as esterification catalysts.

Examples of suitable homogeneous catalysts are mineral acids and esters thereof. These include in particular phosphoric acid, monobutyl phosphate, dibutyl phosphate, monopentyl phosphate, dipentyl phosphate, sulfuric acid, monobutyl sulfate, monopentyl sulfate, hydrogen chloride, p-toluenesulfonic acid, methanesulfonic acid, trifluoromethanesulfonic acid, chlorosulfonic acid and trifluoroacetic acid. 2-keto-L-gulonic acid, diacetone-2-keto-L-gulonic acid or ascorbic acid may also be used as esterification catalysts.

Sulfuric acid, p-toluenesulfonic acid, methanesulfonic acid or a monoalkyl sulfate of the alcohol used is preferably employed. The monoalkyl sulfates eliminate sulfuric acid at above 70° C. [Popelier, Bull. Soc. Chim. Belg. 35 (1926), 265], which then acts as a catalyst. Particularly preferred homogeneous acidic catalysts are sulfuric acid and p-toluenesulfonic acid.

The abovementioned homogeneous catalysts can be either mixed with one of the starting materials before the reaction or fed into the reactor as a separate stream.

Heterogeneous catalysts are advantageously fixed in the hot reaction zone in the reactor. The literature describes numerous possible designs for the installation of heterogeneous catalysts in distillation columns. These include dwell trays, in which the catalyst can be arranged on the trays or in their downpipes, and furthermore coated packings, wound and structured packings with woven-in catalyst.

Suitable heterogeneous catalysts are the acidic catalysts known per se, preferably acidic ion exchangers as well as zeolites.

The term "acid cation exchangers" is to be understood as meaning commercially available resins or detoxans, e.g. Lewatit® S 100, SP 112 or Lewatit® 2631 (Bayer), or Amberlite® 18 and IRA 120 or Amberlyst® 15 or Duolite® C 20, C 26 and C 264 (Rohm & Haas) or Dowex® ion exchangers.

Zeolites are crystalline aluminosilicates which have a highly ordered structure with a rigid three-dimensional network of $SiO_4$ or $AlO_4$ tetrahedra which are linked by common oxygen atoms. The ratio of Si and Al atoms to oxygen is 1:2. The electrovalency of the aluminum-containing tetrahedra is compensated by inclusion of cations in the crystal, for example of an alkali metal or hydrogen atom. Cation exchange is therefore possible. The voids between the tetrahedra are occupied by water molecules prior to dehydration by drying or calcination.

Suitable zeolites are, for example, those of the pentasil type, in particular aluminosilicate zeolites or borosilicate zeolites. By pre-coking, it is possible to adjust the activity of the catalysts for optimum selectivity of the desired reaction product.

According to the invention, the esterification is carried out in a thin liquid film on hot surfaces, the temperature of the surface being from 50 to 250° C., preferably from 80 to 200° C., particularly preferably from 90 to 150° C.

The residence time of the reaction mixture on the hot surface is from 1 to 400, preferably from 20 to 300, particularly preferably from 30 to 250, seconds.

According to the invention, the reaction is carried out at from 1 to 1,000, preferably from 50 to 1,000, particularly preferably from 500 to 950, mbar.

Preferably, the reactors stated at the outset are dimensioned so that complete removal of the water of reaction and hence complete esterification are achieved in short residence times. This ensures that subsequent reactions of the reaction product, for example with the esterification catalyst, are avoided. Preferred apparatuses are the reaction columns known per se, described, inter alia, in Chem. Ing. Techn. 43 (1971), 1101 and having a stripping section and rectifying section, and thin-film evaporators or downflow evaporators.

This method of carrying out the reaction is particularly suitable for esters of 2-keto-L-gulonic acid which do not crystallize spontaneously, e.g. butyl 2-keto-L-gulonate.

In addition to 2-keto-L-gulonic acid, it is also possible to esterify diacetone-2-keto-L-gulonic acid under the abovementioned conditions in the same manner. Elimination of the acetone protective groups additionally occurs. Two mole equivalents of water are required for the elimination, while at the same time one mole equivalent of water is formed in the esterification reaction. In the simplest procedure, the monohydrate of diacetone-2-keto-L-gulonic acid is therefore used. The reaction takes place in the same pressure and temperature range as described above. The acetone formed is distilled off as a low boiler during the esterification reaction, at the beginning or together with excess, water-containing solvent, and can be recycled after isolation and purification and re-used, for example for synthesizing diacetone-2-keto-L-gulonic acid by the classical Reichstein process. When anhydrous diacetone-2-keto-L-gulonic acid is used, 1 mol of water must also be added. 2-keto-L-gulonic acid is preferably used as the starting material for the novel process. The acid may be used either in crystalline form, for example as dried or centrifuge-moist monohydrate, as an anhydrous compound or as an aqueous solution, for example as concentrated fermentation solution.

The monohydrate of 2-keto-L-gulonic acid is obtained, as a rule, in the crystallization from water or water-containing, organic solvents. By centrifuging the crystal slurry, moist monohydrate is obtainable. This can be used as centrifuge-moist product directly in the novel esterification reaction or can be dried under mild conditions.

In the novel process, the drying or dewatering of the monohydrate of 2-keto-L-gulonic acid can advantageously be dispensed with, since azeotropic dewatering is in any case carried out in the subsequent esterification reaction according to the invention.

The conversion of the 2-keto-L-gulonic acid in the esterification reaction in the novel process is substantially above 90%, preferably from 95 to 99%.

The reaction mixture solidifies on cooling in a temperature range of from 30 to 70° C. The melt forms again reversibly and without decomposition on heating The esterification reaction of 2-keto-L-gulonic acid or diacetone-2-keto-L-gulonic acid can be operated batchwise or, preferably, continuously. Under these conditions, too, a molten form of the corresponding alkyl 2-keto-L-gulonate results at the end of the esterification.

In a particularly preferred embodiment of the novel process, an aqueous solution of 2-keto-L-gulonic acid is esterified continuously with n-butanol in the presence of sulfuric acid on a hot surface at from 90 to 150° C. and from 500 to 950 mbar and in a residence time of from 30 to 250 seconds in a thin-film evaporator or in a rectification column.

The alkyl 2-keto-L-gulonate formed can be converted into L-ascorbic acid both under acidic and under basic conditions in a manner known per se.

The novel process has the following advantages:

The esterification reaction can be operated both batchwise and, advantageously, continuously and, particularly when alcohols of more than 3 carbon atoms are used, results in negligible losses of alcohols during the removal of water by distillation.

The residence times are very short in comparison with the processes known from the literature for the preparation of 2-keto-L-gulonic esters, so that as a rule apparatuses of small dimensions can be used The reaction product, for example butyl 2-keto-L-gulonate, can be either isolated directly by conventional methods or used without further isolation for subsequent reactions.

The reaction parameters, such as temperature and feed rate of the starting materials during the esterification, can be adjusted so that the water content and/or the proportion of the esterification alcohol in the reaction mixture tends to zero.

Surprisingly, we have found that in the novel esterification reaction no solid is formed in the reactors, although the keto-L-gulonic acid is sparingly soluble in lower alcohols, e.g. methanol, ethanol, propanol, butanol or pentanol, and the esters formed are present in solvent-free form after the removal of water.

The examples which follow illustrate the novel process.

EXAMPLE 1

Esterification in a Thin-film Evaporator

The experimental apparatus used for the esterification consisted of a glass thin-film evaporator having an evaporator surface of 0.046 m², one vessel each for 2-keto-L-gulonic acid and n-butanol, a mixer zone for the addition of catalytic amounts of sulfuric acid to the feed stream and a distillate vessel and a high-boiler vessel.

An aqueous 2-keto-L-gulonic acid solution was fed continuously to the top of the evaporator at a rate of 12 g/h, together with 660 g/h of n-butanol and a catalytic amount of concentrated sulfuric acid. At 900 mbar, the resulting internal temperature in the evaporator was 110° C. The average residence time of the reaction mixture was about 100 seconds. After a steady state had been established, 10 g/h of a slightly yellowish viscous oil was taken off from the bottom. The reaction product, which consisted of 97% by weight of n-butyl 2-keto-L-gulonate, 0.5% of 2-keto-L-gulonic acid and 2.5% of n-butanol, solidified at 65° C. to give a solid, amorphous material.

By changing the average residence time, the feed rate and the temperature difference in the reaction zone at the evaporator wall, it was possible further to improve the composition of the product mixture in favor of the desired product.

EXAMPLE 2

Esterification in a Reaction Column Without Reactive Internals

The reaction column having an internal diameter of 0.044 m consisted of a rectification section and a stripping section, each 1 m long.

With a feed composition analogous to Example 1, an evaporator temperature of 112° C. resulted at 900 mbar. The reaction product consisted of 98% of n-butyl 2-keto-L-gulonate, 0.1% of 2-keto-L-gulonic acid and 1.9% of n-butanol. It was collected in a vessel kept at 70° C. and then converted into scales on the cooled surface of a scale roller.

EXAMPLE 3

Esterification in a Reaction Column Having a Reactive Section

The esterification was carried out in a laboratory column having a diameter of 0.055 m. The rectification section and stripping section each comprised 4 packed sections, each of max. 0.5 to 1 m with 300 m²/m³. The reactive section was formed by catalyst packing comprising an esterification catalyst (ion exchanger, detoxans, Lewatit® 2631). The apparatus was operated at from 500 to 950 mbar. The pressure drop in the reactive part was 30 mbar.

In the steady state, the conversion was 99.2%. The residual water content was <50 ppm. In addition, small amounts of n-butanol were detectable.

We claim:

1. A process for the preparation of $C_1$–$C_{10}$-alkyl 2-keto-L-gulonates by esterifying 2-keto-L-gulonic acid or diacetone-2-keto-L-gulonic acid with a $C_1$–$C_{10}$-alcohol in the presence of an acidic catalyst, wherein the esterification is carried out in a liquid film on a hot surface with simultaneous removal of water.

2. A process as claimed in claim 1, wherein the esterification is carried out in a thin-film evaporator or in a rectification column.

3. A process as claimed in claim 1, wherein the water is removed by distillation.

4. A process as claimed in claim 1, wherein the residence time of the reaction solution on the hot surface is from 1 to 400 seconds.

5. A process as claimed in claim 1, wherein the esterification is carried out at from 1 to 1,000 mbar.

6. A process as claimed in claim 1, wherein the esterification is carried out on a hot surface at from 50 to 250° C.

7. A process as claimed in claim 1, wherein the esterification is carried out continuously.

8. A process as claimed in claim 1, when the esterification is carried out using a $C_3$–$C_8$-alcohol selected from the group consisting of n-propanol, isopropanol, 1-butanol, 2-butanol, 2-methyl-1-propanol, 2-methyl-2-propanol, 1-pentanol, 1-hexanol and 1-octanol.

9. A process as claimed in claim 1, wherein the esterification is carried out in the presence of a mineral acid, of an acidic ion exchange resin or an acidic zeolite.

10. A process as claimed in claim 1, wherein an aqueous solution of 2-keto-L-gulonic acid is esterified continuously with n-butanol in the presence of sulfuric acid on a hot surface at from 90 to 150° C. and from 500 to 950 mbar and in a residence time of from 30 to 250 seconds in a thin-film evaporator or in a rectification column.

* * * * *